United States Patent [19]

Ribi

[11] Patent Number: 5,552,141
[45] Date of Patent: Sep. 3, 1996

[54] POLYMERIC IMMUNOLOGICAL ADJUVANTS

[76] Inventor: Hans O. Ribi, 1465 Woodberry Ave., San Mateo, Calif. 94403

[21] Appl. No.: 196,950

[22] Filed: Feb. 15, 1994

Related U.S. Application Data

[63] Continuation of Ser. No. 784,923, Oct. 30, 1991, Pat. No. 5,312,620.

[51] Int. Cl.$^6$ ................................................. A61K 39/00
[52] U.S. Cl. ............................. 424/184.1; 424/193.1; 514/772.4
[58] Field of Search ............................ 424/78.31, 88, 424/184.1

[56] References Cited

U.S. PATENT DOCUMENTS 4,455,142  6/1984  Martins et al. ................. 424/184.1
5,312,620  5/1994  Ribi ................................ 424/78.37

*Primary Examiner*—Peter F. Kulkosky
*Attorney, Agent, or Firm*—Bertam I. Rowland

[57] ABSTRACT

Adjuvants for enhancing the immune response to an antigen are provided comprising the adjuvant incorporated into a lipid layer where the adjuvant is covalently or non-covalently involved in a polymeric system. Conveniently, the adjuvant may be conjugated to a polymerizable group and co-polymerized with a water-soluble and/or amphiphilic polymerizable monomer or combined with a polymerized amphiphile. The adjuvant and antigen may then be administered to a mammalian host to obtain enhanced immune response.

2 Claims, No Drawings

POLYMERIC IMMUNOLOGICAL ADJUVANTS

This is a continuation of application Ser. No. 07/784,923 filed Oct. 30, 1991, U.S. Pat. No. 5,312,620.

INTRODUCTION

Technical Field

The field concerns methods and compositions for employing immunization adjuvants to enhance immune responses. The compositions involve various lipids, polymers, and/or polypeptides.

Background

Adjuvants by definition are substances that are incorporated into or are injected simultaneously with an antigen. The adjuvants potentiate non-specifically the ensuing immune response. A principal purpose for employment of an immunotherapeutic adjuvant is to achieve more durable humoral or cell-mediated immunity of a high level by employing lower levels of an antigen with fewer numbers of doses than could be achieved by administering the equivalent aqueous antigen. Adjuvants are used in combination with non-living agents (in place of living microorganisms), for the preparation of vaccines. Adjuvants may also increase the effective immune response against low or nonimmunogenic tumor cells or cells infected with intracellular agents that are already present in the body and are not adequately checked by naturally elicited immune responses.

As studies slowly unravel the cellular and molecular mechanisms responsible for host immune responses, the challenge to design new compounds necessary to modulate both humoral and cell-mediated immunity becomes increasingly apparent. While hypotheses have been proposed as to how adjuvants augment the immune response, no substantial evidence exists which supports any particular theory or provides for a predictive rationale which can serve as a basis for designing improved adjuvants. To that extent then, while one can extrapolate from adjuvants which have been shown to be successful, there is still substantial uncertainty as to whether there will be success with new compositions.

With the advent of genetic engineering, there is now the possibility to develop any protein molecule, which can be used to mimic an epitope of an antigen of interest. For the most part, proteins by themselves do not elicit strong immune responses, as compared to a cell containing such protein. There is, therefore, an increased interest in being able to develop adjuvants which will potentiate immune responses to proteins or other antigenic compositions, e.g. saccharide or hapten conjugates, so as to produce neutralizing antibodies or cell-mediated immunity effective for protecting a host against a pathogen.

Relevant Literature

Ribi, Structure-Function Relationship of Bacterial Adjuvants, In: *Advances in Carriers and Adjuvants for Veterinary Biologics*, Netrig, Gough, Kaeberle and Whetstone, eds., Iowa State University Press, Ames, Iowa, 1986, p. 35–49, describes improvements in bacterial adjuvants.

Other references of interest concerning adjurants include Ribi et al., *J. Natl. Cancer Inst.* (1975) 55:1253; Ribi, *J. Biol. Resp. Mod.* (1984)3:1–9; Ribi et al., BCG Cell Wall Skeleton, P3, MDP and Other Microbial Components-Structural Activities in Animal Models, In: *Augmenting Agents In Cancer Therapy*, Hersh, Chirigos and Mastrangelo, eds., Raven Press, New York, 1981, p. 15ff; Ribi et al., *Rev. Infect. Dis.* (1984) 6:567–572; Takayama. et al., *Rev. Infect. Dis.* (1984) 6:439; Chase et al., *Inf. and Immun.* (1986) 53:71; Ribi et al., Modulation of Humoral and Cell-Mediated Immune Responses by a Structurally Established Nontoxic Lipid A, In: *Proc. Symp. on Bacterial Endotoxins*, Tampa, Fla, Jan. 1985; Immunology and Immunopharmacology of Bacterial Endotoxins, Plenum Publishing Inc., N.Y., 1986, p 407; Ribi et al., Immuno Potentiating Activities of Monophosphoryl Lipid A, In: *Int. Sym. on Immunological Adjuvants and Modulators of Nonspecific Resistance to Microbial Infections*, Columbia, Md., July 1986, Alen Liss Inc., N.Y., 1986; Ribi et al., Enhancement of Tumor Immunity with Bacterial Adjuvants, In: *Development in Industrial Microbiology*, vol. 27, supp. 1, 1987, p. 19; Tomai et al., *J. Bio. Resp. Mod.* (1987) No. 6, 99; and Philip et al., *Cancer Res.* (1985) 45:128–134.

References related to the polymerization of lipids and drugs include Ringsdorf, *J. Polym. Sci.* (1975) Symp. No. 51, 135; Przybylski et al., *Makromol. Chem.* (1978) 179:1719; Hirano et al., *Tetra. Lett.* (1979) 10:883; Hirano et al., *Cancer Research* (1980) 40:2263; Gros et al., *Angew. Chem. Int. Ed. Engl.* (1981) 20:305; Kobayashi et al., *Makromol. Chem.* (1983) 184:793; Bader et al., *Angew. Makromol. Chem.* (1984) 123/124:457; Pratten et al., *Makromol. Chem.*, (1985) 186:725; Elbert et al., *J. Am. Chem. Soc.* (1985) 107:4143; Sackmann et al., *Ber. Bunsenges. Phys. Chem.* (1985) 89:1208; Dorn et al., Polymeric Antitumor Agents on a Molecular and Cellular Level, In: *Bioactive Polymer Systems, An Overview*, Gebelein and Carfaber, eds., Plenum Press, N.Y., 1985, 19:531; and Matsumura and Takahashi, *Makromol. Chem. Rapid Commun.* (1986) 7:369.

Gaub et al., *Biophys. J.* (1984) 45:725–731; Laschewsky et al., *Die Angewandte Makromolekulare Chemie* (1986) 145/146:1–11; Frey et al., *Macromolecules* (1987) 20:1312–1321, describe the physical properties of polymerized and copolymerized amphiphiles. See also, Gotbach et al., *Bioorganicheskaya Khimiya* (1985) 11:671–673.

SUMMARY OF THE INVENTION

Polymeric immunologically active adjuvants and methods of use are provided, where the adjuvants may be used in immunotherapeutic applications or production of antibodies. The polymeric adjuvants comprise a pharmacologically acceptable lipid where the adjuvant is covalently or non-covalently associated with the polymer. Polymeric lipid-adjuvants take the form of lipid layers or colloidal particles. The polymers may be prepared in a variety of ways and the polymeric product administered separately or in combination with an immunogen.

DESCRIPTION OF THE SPECIFIC EMBODIMENTS

Immunotherapeutic adjuvants are comprised of polymer-containing lipid layers which may be present in a colloidal form (e.g. vesicles). The lipid layers include the adjuvant active component. The adjuvant active component may be the lipid layer forming component, or covalently or non-covalently associated with the lipid layer forming component. Depending upon the polymer, the adjuvant active compound may be covalently bonded to the polymer or non-covalently associated with hydrophilic or hydrophobic portions of the polymer.

Bacterially derived immune modulators (adjurants) exist naturally within the polymer matrix of bacterial cell walls. Isolated and detoxified forms of these adjuvants have been shown to retain many of their beneficial properties. Monomeric forms of bacterial adjuvants are, however, unstable and exhibit reduced half lives. Repolymerization of purified forms of these adjuvants, thus serves several objectives: first, to reconstitute the adjuvant component into a relevant context, a polymer form; second, to allow for flexibility in the polymeric composition, in order to vary the physical/ chemical properties of the system in vivo; and third, to provide for more stable adjuvant formulations (during storage and in vivo).

The polymeric adjuvant composition will comprise at least one polymerized lipid moiety having at least three monomeric units. The compostion will include at least one of a lamellar forming lipid adjuvant and, possibly, a lamellar forming "non-adjuvant" lipid, where with the "non-adjuvant" livid, the adjuvant will be present either co-polymerized or linked to a lipid. By "non-adjuvant" is intended a lamellar forming lipid which by itself does not enhance immune response to an antigen. By lamellar forming is intended self-organizing lipids which are able to form stable mono-or multilayers in solution or at interfaces.

Polymeric adjuvant systems serve several purposes: first, to potentiate and regulate beneficial immune responses; second, to provide a high degree of colloidal stability and half life of the adjuvants both before and after injection into the host; and third, to create a controllable adjuvant release system (a depot) which avoids the use of oils which may cause toxic side effects to the host.

The adjuvants for the most part will comprise at least one lipid or peptide and at least one polyol, usually a sugar, e.g. an aminosugar, such as muramic acid or a disaccharide such as trehalose or glucosamine disaccharide; or glycerol, e.g. phosphatide, phosphoinositide diglycerol ether, etc. Illustrative adjuvants include monophosphoryl lipid A (MPL), diphosphoryl lipid A (DPL), muramyl dipeptide-phosphatidylethanolamine (MDP-PE), muramyl tripeptide-phosphatidylethanolamine (MTP-PE), mycolic acid (e.g. arabinomycolate), trehalose monomycolate, trehalose dimycolate (TDM), lipid X (LX), or other adjuvant forms such as isoprinosines and plant lithospermans.

The polymer and adjuvant-containing compositions involve an adjuvant covalently bonded to a polymerizable monomer or covalently bonded to lipid. The polymeric compositions will involve adjuvant-lipid conjugate monomer combined with polymeric lipid; adjuvant-(polymerizable monomer) oligomer combined with polymeric or non-polymeric lipid; adjuvant-(polymerizable monomer) copolymerized with polymerizable lipid; and adjuvant(lipid)-(polymerizable monomer) polymerized with non-lipid monomer. In all of the compositions, the adjuvant will be flexibly associated with the polymer, such as through non-covalent lipid association, linkage through a flexible, usually long aliphatic, hydrophilic chain and/or adjuvant-polymerizable monomer conjugate copolymerized with hydrophilic monomer to provide a significant spacer between adjuvant conjugate monomers in the polymer. Thus, either the adjuvant or the lipid may be monomeric or polymeric and where adjuvant is lipophilic, no other lipid need be employed, unless to modify the composition.

The polymers may be any convenient oligomer for incorporating the active adjuvant component. The polymers may be natural or synthetic polymers or combinations thereof, the polymer usually having at least about 3 units and may have 10,000 or more units, the size of the polymer not being critical to this invention, but rather associated with ease of formulation and administration, as well as physiological acceptability. The polymers may be biodegradable or non-biodegradable.

The polymers may be polyesters, polyacrylates, polyethers, polypeptides, polyolefins, polyacetylenes, particularly polydiacetylenes, polyenes, polyamides, disulfides, polysilanes and polysilynes, polycyano compounds, or the like. The polymeric backbone may include such heteroatoms as oxygen, sulfur, nitrogen, silicon, phosphorus, or the like.

The polymers may be addition or condensation polymers, usually addition polymers. Functionalities which may be present include aliphatic unsaturation-olefins or acetylene—esters, both organic and inorganic, ethers, both oxy and thio, amides, hydroxy, amino, nitro, cyano, etc. The polymers may be a backbone polymer with lipid groups pendant from the backbone or the polymer may involve polymerization of the lipid groups e.g. through polyunsaturation, or the like.

Illustrative polymers include acrylic or methacrylic acid polymers, particularly derivatives thereof, such as amides and esters, both as homo- or copolymers, having side groups, such as hydroxyethyl, aminopropyl, methyl, ethyl, 2-aminoethyl, 2-ammoniumethyl, or the like; polyvinyl alcohol and esters thereof, e.g. acetate or fatty acids of from about 8 to 100 carbon atoms, particularly of from about 12 to 30 carbon atoms; polydiacetylenes, particularly where the diacetylenes are internal to aliphatic chains of at least about 8 to 60 carbon atoms, more usually up to about 30 carbon atoms; substituted polybutadiene or polyisoprene; polysuccinates, employing glycols of from about 2 to 10 carbon atoms; polyamides, such as poly-adipamide or polysuccinamide with a diamine of from about 2 to 10 carbon atoms where from about 1 to 20 mol % of the monomers which do not have functionalities for attachment may be substituted for a monomer having a site for attachment, e.g. succinic by maleic or fumaric, propylene glycol by dihydroxyacetone, isoprene by 2-carboxymethylbutadiene, polydisulfides, with the sulfhydryl moieties attached to the aliphatic chains or polar groups, etc.

Self-organization .of polymeric adjuvants into stable colloidal structures may further require co-polymerization of the adjuvant with small polymerizable molecules (co-monomers, usually hydrophilic). Co-polymerization allows the spacings between adjuvant molecules, along any given polymer chain, to be regulated by varying the mol percentage of the co-monomer. Oriented monolayers, multilayers, and vesicles have been prepared by this approach (Laschewsky, A. et al., supra; Frey, W. et al., supra).

It may be desirable for the hydrophilic-polymerizable co-monomer to include a hydrophilic adjuvant such as MDP or MTP derivatized with a polymerizable group (e.g. acryl, methacryl, 2-hydroxethyl-acrylate, etc.). Co-polymerization of a hydrophilic adjuvant with a lipophilic adjuvant, bearing a compatible polymerizable group, provides for the formation of mixed polymeric adjuvants which are both stabilized by the polymeric backbone and able to self-assemble into colloidal structures. Alternatively, mixed adjuvant systems may be comprised solely of various lipophilic adjuvants co-polymerized on the same polymer backbone (heteropolymers) or each polymerizable adjuvant may be polymerized individually (homopolymers) and then mixed together.

The polymers will have a lipid or hydrophobic group present in a ratio of at least one aliphatic chain of at least 8 carbon atoms per 100 monomer units, and there may be 2 or more hydrophobic chains per monomer unit. The number of lipid groups will be selected to provide for a stable colloidal particle (lipid layers, including vesicles as appropriate).

The active adjuvant entity may be present as part of the polymer as being covalently bonded directly or through a linking group to a functionality present on the polymer backbone or may be non-covalently associated with the hydrophobic groups of the polymer in the lipid layer. For covalent linkage of the adjuvant to the polymeric backbone, monomers which do not have a convenient functional group, may be chemically modified to introduce an occasional functional group for linking the adjuvant to the polymer in an appropriate ratio.

Introducing polymerizable groups into adjuvant molecules involves chemically modifying the adjuvant without perturbing the adjuvant's beneficial properties. Polymerizable moieties are introduced through covalent attachment to functional groups at various positions on the adjuvant. This can be achieved in a variety of ways, such as providing for olefinic groups for coupling with a mercaptan, hydroxyl groups to form esters and ethers, amino groups, to provide for amides or alkylation, for example with an aldehyde under reductive amination conditions. Usually the linking site will be the hydroxyl group of a sugar or through an amino group of a sugar or side chain. For separating the polymerizable group from the adjuvant and to provide for flexibility in the polymer chain, spacer groups may be employed. The spacers facilitate the polymerization process and allow the adjuvant to function in a relevant context, without interference from the polymer backbone. It is often desirable to attach spacers and polymerizable groups at different positions on the adjuvant, depending upon the chemical structure of the adjuvant, type of polymerizable group, polymer structure of interest, and effect that the polymer backbone may have on the adjuvant's properties.

The linking group may be any bifunctional group which allows for linking of the adjuvant to the polymeric backbone. Of particular interest will be those linking groups which include such functionalities as hydroxyls, halogens, aminos, carboxyls, thiols, phosphoroyls, or the like. The linking group will usually have at least one carbon atom, more usually at least two carbon atoms and could have 100 carbon atoms or more, the chain being a matter of convenience. Usually, the chain will be 20 carbons or fewer, preferably 12 carbons or fewer. The linking group may be aliphatic, alicyclic, aromatic or heterocyclic, or combinations thereof. The linking group may be aliphatically saturated or unsaturated, usually having fewer than about two sites of unsaturation, and may be hydrophobic or hydrophilic. Illustrative linking groups include hydroxyamines, such as ethanolamine, saccharides, such as glucose, fructose, ribose, etc., ethylene or polyethylene glycols (oxides) or homologs thereof, e.g. mono- or polypropylene glycols, alkyl diamines such as propylene diamine or 1,6-diaminohexane, dicarboxylic acids such a maleic, fumaric, succinic, adipic, suberic, etc., hydroxy or amino acids or peptides, such as glycolic acid, 6-aminohexanoic acid, di- or triglycine, cysteine, etc., or the like.

The adjuvant monomer may or may not have lipid moieties. Non-lipid adjuvants may be chemically coupled to a lipid to provide for an amphiphilic molecule. The lipid molecules may be conjugated to a variety of hydrophilic monomers, particularly addition polymerizable monomers.

Illustrative hydrophilic adjuvant monomers, which may be coupled to polymerizable lipids, include various muramyldipeptides (e.g. N-acetylmuramyl-L-threonyl-D-isoglutamine or N-acetylmuramyl-L-theonyl-D-isoglutamine). Hydrophilic adjuvant monomers derivatized with a polymerizable moiety (e.g. $N^1$-(N-acetylmuramyl-L-alanyl-D-isoglutaminyl)-$N^6$-actyloyl-hexamethylenediamine, or $N^4$-(N-acetylmuramyl-L-alanyl-D-isoglutaminyl)-N-triglycylacrylamide), may be coupled to a non-polymerizable lipid.

Illustrative lipophilic adjuvants, modified with polyermizable moieties include lipid A derivatives, such as tetraethyleneglycolacrylate-ether-$O^6$-monophosphoryl lipid A, and trehalose dimycolate derivatives, such as vinylether-tetraethyleneglycol-ether-trehalose dimycolate.

Illustrative polymerizable lipid monomers include stearyl acrylate, hexadecyl acrylate 2,3-Bis(hexadecanoyloxy) propyl-9-methacryloyl- 3,6,9-trioxanonyldimethammonium iodide, 12-methacroyl- 3,6,9,12-tetraoxadodecyl 3-(N,N-dioctadecyl carbamoyl) propionate, sodium 2,3-bis(hexadecyloxy)propyl-12 -methacroyl-3,6,9,12-tetraoxadecylphosphate, dioctadecadienoyl-bis(dihydroxyethyl) dimethylammonium bromide, or the like (see Relevant Literature).

Of particular interest are polymers which involve surfactants and are cap able of forming lamellae, more particularly as vesicles. The vesicles may be small or large, generally from about 200 Å to 100 μ in diameter, and may be unilamellar or multi-lamellar, being single or multichamber. Alternatively, the lipophilic polymers may be prepared as layers, in the form of micelles, tubes, helices, planar arrays, and linear or filamentous structures.

The surfactant groups may be phosphatides, where at least one lipid chain will be at least 8 carbon atoms, usually at least about 12 carbon atoms and not more than about 100 carbon atoms, more usually not more than about 36 carbon atoms. The surfactants may include phosphatides, phosphatidyl sugars, ethanolamine, choline, inositol, glycerol, alkylamines, etc. The surfactants may be fatty acids, amines, ethers, esters, alcohols, cardiolipins, lipid-nucleotides, gangliosides, cerebrosides, halogenated chains, particularly halogen of atomic numbers 9 to 80, more particularly 9 to 35, glycolipids, lipoproteins, mycolares, tetraalkylamines, archeo-type lipids (dual-headed), lipopolysaccharides, or the like, where the lipid moieties will be at least 8 carbon atoms and usually not more than about 100 carbon atoms, more usually not more than about 36 carbon atoms, primarily as a matter of convenience rather than necessity, lipids being readily available in this carbon number range. Usually, there will be at least about 1 percent of the polymeric units carrying a lipid group, more usually at least about 5 percent and generally from about 10 to 100 percent of the polymeric units will carry a lipid group. The lipid adjuvant will be present in at least about 0.01 weight percent, more usually at least about 1 percent and may be as high as 90 percent, usually being not more than about 50 percent, more usually being not more than about 25 weight percent of the lipid composition.

Polymer forming lipids may be found in Elbert et al., *J. Am. Chem. Soc.* (1985) 107:4134–4141, as well as other references cited previously, e.g. Frey et al., Laschewsky et al., and Bader et al., where fatty acid esters of glycerol or other polyols are linked through hydrophilic linking groups or spacers to a polymerizable hydrophilic moiety. This same approach may be employed in the subject invention by combining a lipophilic adjuvant with the polymerizable lipid monomer for non-covalent association of the adjuvant with the polymer. Alternatively, the adjuvant may be modified with an acrylic group or other polymerizable group, through a hydrophilic linker, and then incorporated covalently in the polymer and lipid layer. Other polymers such as polydiacetylenes may be employed (see, for example, co-pending application Ser. No. 933,034 filed Nov. 20, 1986).

For enzymatic condensation polymerization, procedures such as the one of Matsumara and Takahashi, *Makromol. Chem. Rapid Commun.* (1986) 7:369–373, may be employed. Hydroxyacids having lipid side groups may be polymerized, employing such acids as 12-hydroxyoctadecanoic acid, 12-hydroxy-cis-9-octadecanoic acid, 16-hydroxyhexadecanoic acid and 12-hydroxydodecanoic acid. The enzyme which catalyzes the reaction is obtained from *Candida rugosa* and is commercially available from Sigma Chemical Co., St. Louis, Mo. The resulting oligomers may be combined with adjuvants to form vesicles or the adjuvant may be linked through an available hydroxyl group to a free carboxyl group of the oligomer, using activating agents such as carbodiimides, e.g. dicyclohexylcarbodiimide, or carbonyl diimidazole. Also oil-in-water emulsions may be employed. The monomer hydroxy acids may also be coupled to the adjuvant before enzymatic polyermization.

To reduce the risk of toxic side effects, which may result from non-natural polymers (Bonte et al., *Biochim. Biophys. Acta* (1987) 900:1–9), it may be desirable to use biodegradable polymers as the basis for the polymer-adjuvant backbone. One example of a biodegradable polymeric adjuvant is prepared by incorporating at least two sulfhydryl moieties into the adjuvant. Upon mild oxidation, the sulfhydryl groups form intermolecular disulfide bridges which crosslink the adjuvant and/or polymerizable "filler" lipid, into linear or two-dimensional polymers. Approaches for preparing sulfhydryl-linked phospholipids ape reported elsewhere (Bonte, et al.; Weber, et al.).

In preparing the polymerized surfactant layer, the polymerizable surfactant, for example, is dissolved in a convenient volatile solvent, e.g. non-polar, by itself, or in combination with the adjuvant. Illustrative solvents include chloroform, hexane, isopropyl ether, methylenedichloride, benzene, ketones, etc. Individual solvents or combinations may be employed, depending upon the nature of the monomeric surfactant or adjuvant. Trace amounts of an organic hydrophilic solvent may be employed (e.g. methanol, ethanol, dimethyl sulfoxide, etc.) when necessary to solubilize a particular monomer. The concentration of monomeric surfactant will generally be from about 0.01 to 50, more usuallly about 0.5 to 10 mg/ml.

Depending upon the nature of the polymerizable functionality, the monomeric surfactant may now be polymerized. Polymerization is accomplished with the lipids suspended in an aqueous solution, dissolved in an organic solvent, or dried into a paste form. Depending upon the desirability for mobility of the adjuvant in the layer, the polymerization may be carried out below the transition melting temperature of the lipid to provide for immobility of the acyl chains. The polymer may have as few as 3 units or may have $10^7$ or more units. Polymerization may be achieved by employing short wave ultraviolet light, e.g. below 300 nm, with diynes, usually in the range of about 230 to 275 nm, X-rays, electron beams, free radicals, redox agents, or other convenient initiators. The time for the polymerization (irradiation, for example, will be at least about 1 min) will usually be not more than several days, frequently not more than about 6 hr, more usually not more than about 90 min.

The lipophilic polymers and adjuvants, as appropriate, may be mixed with other lipids to form the adjuvant composition, particularly as vesicles. These lipids will be surfactants, comprising a polar or charged terminus joined to a lipophilic chain, usually an aliphatic chain of from about 8 to 100 carbon atoms or more. These filler surfactants may be monomeric or polymeric. If the adjuvant and surfactant are polymeric, they may be bonded to the same or different polymer chain. The monomeric lipids may include: phosphatidylethanolamine, phosphatidylcholine, phosphatidylinositols, phosphatidylglycerol and mono- or dimethylphosphatidylethanolamine, fatty acids, amines, ethers, esters, alcohols, cardiolipins, gangliosides, lipid nucleotides (Ribi et al., *Biochemistry* (1987) 26:7974–7976), cerebrosides, halogenated chains, glycolipids, lipoproteins, mycolates, tetraalkylamines, archeo-type lipids, steroids, e.g. cholesterol, and any other naturally occurring, synthetic surfactants or combinations thereof. The lipids may be compositions from natural sources, such as plant, bacterial, etc.

In many instances, it may be desirable to have an entity of interest Joined to either the adjuvant, the adjuvant containing polymer or the filler surfactant containing polymer. These additives may be involved in ease of isolation of the polymeric product, e.g. liposome, targeting to a particular cell type or site, binding of the polymer to another polymer, forming complexes with other entities, or the like. Thus, any ligand may be Joined to the polymer, where the ligand may include nucleotides, oligonucleotides, peptides, enzymes, toxins, phosphates, saccharides, phthalocyanines, drugs (monomeric or polymeric), amino acids, chromophores, natural ligands such as biotin, lectins, bifunctional reagents, effector molecules, sugars, antigens, dyes, crown ethers, silanes, steroids, haptens, radioactively labelled moieties, chelating agents or the like.

The system allows for great flexibility in bringing together a variety of moieties which may serve individual functions, while providing for adjuvant activity. Thus, oligonucleotides may be employed, which may then be complexed specifically and non-covalently with large nucleic acid polymers. In this manner, monomeric units may be prepared, which may be non-covalently bonded to a large polymer to provide for side chains which may be the same or different. Chromophores may be included which may be used to monitor concentration, size of particles, numbers of liposomes, etc. Ligands such as biotin may be employed, which may be used for binding to avidin or streptavidin ("avidin"), for bringing together multiple groups, for separation or the like.

By employing various mixtures, one can modify many of the adjuvant's properties. By using the adjuvant, or adjuvant polymer, by itself or in conjunction with the filler surfactants, one may control morphology and more closely mimic natural biological cell walls. In addition, by preparing vesicles, one may encapsulate drugs within the vesicle, which may act to stimulate or retard cell growth. For example, one could be interested in stimulating B-cell proliferation with mitogens, while suppressing T-cell types with suppressing agents. By employing cleavable linkages, where the linkage is cleaved under physiologic conditions, including enzymatic hydrolysis, one can carry a variety of compounds, such as drugs or prodrugs, with the adjuvant polymer or the polymeric filler surfactant. These drugs may serve to selectively inhibit T-cells as opposed to B-cells. In addition, drugs may be included in the polymer by linking to a monomer through a physiologically cleavable linkage.

It may be necessary to employ combination therapies such as immunotherapy-chemotherapy. To this extent, the polymer-adjuvant system may be functionally modified to contain chemotherapeutic drugs. Alternatively, the drugs may be encapsulated within the polymer-adjuvant vesicles. Liposomal encapsulation has been shown to reduce the toxicity of several chemotherapeutic agents. The drugs may be covalently or non-covalently associated with monomeric or polymeric filler surfactants or adjuvants. The mol ratios of chemotherapeutic drugs to adjuvants may be controlled by chemical introduction of specific functional groups at desired locations on the polymer backbone or on the monomeric sufactants. The chemotherapeutic drug may also be incorporated directly into the polymer backbone. For example, methacrylalannomycin, prepared as described (Molz, Ph.D. Dissertation, Mainz, West Germany (1982)), may be co-polymerized with a methacryl-containing adjuvant or co-polymerized with the filler surfactant. Each configuration provides for the slow sustained release of both the adjuvant and chemotherapeutic drug.

Another approach involves the non-covalent association of a chemotherapeutic drug with the polymeric adjuvant system. Adriamycin, for example, which is known to associate with cardiolipin (Goormaghtigh et al., *Biochemistry* (1987) 26:1789–1794), may be complexed with polymeric adjuvant liposomes containing cardiolipin.

The physical state of the polymeric adjuvant system may be modulated by choosing surfactants (polymerizable or non-polymerizable) with the appropriate acyl chain composition and configuration. For example, butadiene, methacryloyl and sulfhydryl-linked lipids may be polymerized and remain stable in a fluid state, whereas diacetylenic lipids require crystallinity for polymerization. The lipid phase state was shown to be critical for the binding of anti-lipid antibodies (Rauch et al., *J. Biol. Chem.* (1986) 261:9672–9677). Lateral phase separation of various adjuvant of filler surfactant compositions may be desirable under certain circumstances. Co-existing solid-liquid or monomer-polymer phases may play a role in controlling the proper delivery of adjuvants into the host. Furthermore, the dimensions and morphologies of colloidal aggregates of the lipids (e.g. tubular, helical, filamentous, hexagonal phase, uni- or multilamellar, etc.) may be controlled by varying the lipid composition.

Depending upon the nature of the composition, the subject compositions may be prepared in a variety of ways. Vesicles may be prepared in accordance with conventional techniques, by combining the adjuvant polymer by itself, or in combination with filler surfacants in an appropriate aqueous medium, subjecting the medium to agitation, e.g. sonication, or slow swelling, for sufficient time to form liposomes or other colloidal aggregates, followed by removal of the medium. For techniques for preparing liposomes, see, for example, U.S. Pat. Nos. 4,311,712; 4,310,506; 4,302,549; 4,261,975; 4,241,046; 4,235,871; and 4,299,360. For forming tubes or other structural entity, see, for example, co-pending application Ser. No. 933,034, filed Nov. 20, 1986; and Ribi et al., *Biochemistry* (1987) 26:7974–7976. For forming layers, which may be mono-, bi- or higher order, see, for example, Sugi, *J. Mol. Electronics.* (1985) 113–17; Bader et al., *Adv. in Polymer Sci.* (1985) 64:1.

The subject adjuvants may be combined with the immunogen in a physiologically acceptable medium in accordance with conventional techniques for employing adjuvants. Various media include water, phosphate buffered saline, aqueous ethanol, dimethyl sulfoxide, other buffers which may contain trace amounts of triethylamine or other molecules which may aid in solubilizing the composition. Generally, the immunogen will be present in from about 0.01 µg to 1000 µg, more usually from about 5 µg to 100 µg. The adjuvant will be present, based on the immunogen in from about 0.1 to 100 mol ratio, more usually from about 1 to 10 mol ratio.

Polymeric adjuvant systems are amenable to use in conventional adjuvant delivery systems. While the subject invention is preferably used without oils, in some instances the use of oils may be acceptable. For example, polymer-adjuvants may be mixed with squalene oil in oil-in-water emulsions (see cited literature) and administered by injection into the host. Ultimately it may be beneficial to eliminate the use of oils completely.

Rather than mixing the immunogen with the adjuvant, the immunogen may be covalently or non-covalently reacted with the adjuvant. By having receptors for the immunogen bound to the vesicles or lipid layer, the immunogen may become non-covalently bound. Alternatively, as described previously, cross-linking or bridging agents may be employed for bonding the immunogen to a lipid unit in the layer. When the immunogen is included in the medium during preparation, it may be captured in the lumen and depending on the immunogen, or may be exposed at the surface of the vesicle.

The resulting formulation may be administered in a single administration or multiple administrations spaced from about 3 days to a month or more apart. The administration may be parenteral, topical, with the aid of transdermal patches, subcutaneous, peritoneal, intravascular, oral, by inhalation, or the like. The particular method of administration is not critical to this invention.

The wide range of polymeric adjuvant formulations and various means of preparation and polymerization provide for great versatility in design and function. Several configurations of polymeric adjuvant systems follow: I) lipophilic adjuvants (naturally occurring, chemically modified, semi-synthetic, or fully synthetic), derivatized with polymerizable moieties, are mixed with monomeric surfactants to form stable lamellar; II) polymerizable lipophilic adjuvants are co-polymerized with lipophilic surfactants; III) polymers of lipophilic adjuvants are mixed with polymers of lipophilic surfactants; IV) polymerizable lipophilic adjuvants are co-polymerized with polymerizable hydrophilic adjuvants; V) monomeric non-polymerizable lipophilic adjuvants are mixed with polymeric surfactants; VI) lipophilic polymeric adjuvants of various combinations are mixed alone or in combination with monomeric adjuvants with conventional oil-in-water emulsion systems (see relevant literature); and various combinations thereof. Polymerization of a particular system may be carried out with the lipids in a lamellar state, amorphous glassy state (neat) or with the monomers solubilized in an organic solvent. Polymerization, as mentioned earlier, may be initiated by a774 number of methods. A wide range of polymerizable surfactants that may serve as fillers has been reported (Bader, H. et. al., Advances in Polymer Membranes In: *Polymer Membranes* 64 (1985) (Gordon, M. ed.) Springer Verlag, New York; Fendler, *Science* (1984) 223:888). In each case adjuvants are incorporated into stable polymerized assemblies of colloidal dimensions. The polymerized adjuvant systems may be used alone or in combination with antigen (vital, bacterial, tumor or the like) for the treatment of malignant or infectious diseases through non-specific or specific immunotherapy.

The following examples are offered by way of illustration and not by way of limitation.

EXPERIMENTAL

Preparation of Lipophilic Adjuvants Linked to Polymerizable Moieties through Hydrophilic Spacers Synthesis of the polymerizable-linker 12-methacryloyl-3,6,9,12-tetraoxadecyl-succinate (MTS):

A solution containing methacroyl chloride ($1.0 \times 10^{-2}$ mol) and dry dioxane (30 ml) is added dropwise to a solution containing tetraethyleneglycol ($2.0 \times 10^{-2}$ mol), diisopropylamine ($1.0 \times 10^{-2}$ mol) and dry dioxane (30 ml) stirring at 10° C. After 30 min the reaction is warmed to 23° C. and stirred for 40 min. The solvent is removed in vacuo, the residuum resuspended in diethyl ether, extracted twice with double glass distilled water, and then the organic phase is allowed to dry over magnesium sulfate. The solvent is removed in vacuo and then the product, methacryloyltetraethyleneglycol, purified by reverse phase column chromatography.

Methacryloyltetraethyleneglycol ($5 \times 10^{-3}$ mol), stirring at 40° C. in dry dioxane (20 ml) and triethylamine ($5 \times 10^{-3}$ mol), is succinylated with succinic anhydride ($5 \times 10^{-3}$ mol). The solvent is removed in vacuo and the product, 12-methacryloyl- 3,6,9,12-tetraoxadecyl-succinate (MTS), used directly or further purified by reverse phase column chromatography. The product is characterized by Liquid Secondary Mass Spectrometry (LSIMS), $H^1$-NMR, and IR.

Synthesis of 12-methacryloyl-3,6,9,12 -tetraoxadecyl-succinyl-$O^6$-monophosphoryl lipid A (MTS-MPL):

MTS (42 mg, $1.2 \times 10^{-4}$ mol) is dissolved in dioxane (2 ml). After the addition of dicyclohexyloarbodiimide (36 mg, $1.7 \times 10^{-4}$ mol) the solution is stirred at 40° C. for 10 min and then let stand at 23° C. for 1 hr. A precipitate of dicyclohexyl urea is removed by filtration through glass wool, and the filtrate added to a solution containing monophosphoryl lipid A (100 mg, $-5.82 \times 10^{-5}$ mol), prepared as described (Ribi et al., *Cancer Immun. Immunotherap.* (1982) 12:91–96; Qureshi et al., *J. Biol. Chem.* (1982) 257:11808–11815; Ribi et al., *Rev. Infect. Dis.* (1984) 6:567–572), triethylamine (0.016 ml), and 2 ml dichloromethane. After stirring at 23° C. for 8 hr, half of the solvent is removed in vacuo and the remaining mixture fractionated by liquid column chromatography (silica gel) using a chloroform:methanol:water:ammonium hydroxide gradient. The solvent is removed in vacuo and the product, 12-methacryloyl-3,6,9,12-tetraoxadecylsuccinyl-$O^6$-monophosphoryl lipid A, is characterized by LSIMS, $H^1$-NMR, and IR.

Synthesis of N-acetylmuramyl-L-alanyl-D-isoglutamylaminocaproyl-di-( 10, 12-nonacosadiynoyl)-phosphatidylethanolamine (MDP-aminocaproyl-DNDPE):

t-BOC-aminocaproic acid (93 mg, $4.0 \times 10^{-4}$) prepared as described (Moroder et al., *Hoppe-Seyler's Z. Physiol. Chem.* (1976) 1651–1653), and dicyclohexylcarbodiimide (167 mg, $8.1 \times 10^{-4}$ mol) are combined in 3.0 ml of dry dichloromethane and stirred at room temperature for 40 min. The precipitate of dicyclohexyl urea is removed by filtration through glass wool, and the filtrate added to 104 mg ($1.0 \times 10^{-4}$ mol) of di(10,12-nonacosadiynoyl)-phosphatidylethanolamine (DNDPE) in 1 ml of dry dichloromethane and 150 µl of dry pyridine. The mixture is stirred for 2 hr and then applied to a column of silica gel. The column is washed with chloroform:acetone (1:1 v/v) and eluted with chloroform:methanol under low pressure (10 psi). The solvent is removed in vacuo yielding 85 mg of t-BOC-aminocaproyl-DNDPE. Infrared (KBr pellet): bands at 1660 cm$^{-1}$ (carbonyl) and 3400 cm$^{-1}$ (amide).

The amino-protecting group is removed from 85 mg of t-BOC-aminocaproyl-DNDPE by stirring in a solution of 33% trifluoroacetic acid and 67% dichloromethane (5 ml) for 1–3 hr at 25° C. Solvents are removed in vacuo, and the residue fractionated on a silica gel column, yielding 60 mg of aminocaproyl-DNDPE. Digestion with phospholipase $A_2$ demonstrates an intact phospholipid by conversion to a lysophospholipid. Infrared (KBr pellet): bands at 3350 and 3210 cm$^{-1}$ (amine).

N-acetylmuramyl-L-alanyl-D-isoglutamine (50 mg, $1 \times 10^{-4}$ mol) prepared as described (Schwartzman et al., *Preparative Biochemistry* (1980) 10 (3) :255–267), and dicyclohexylcarbodiimide (31 mg, $1.5 \times 10^{-4}$ mol) are combined in 1.5 ml dioxane: dichloromethane, stirred at 23° C. for 10 min, and then allowed to settle for 1 hr. The precipitate of dicyclohexyl urea is removed by filtration through glass wool, and the filtrate is added to a solution containing aminocaproyl-DNDPE (58 mg, $5 \times 10^{-5}$ mol), triethylamine ($6 \times 10^{-5}$ mol), and 1.5 ml dioxane: dichloromethane. After 6 hr. the reaction mixture is purified by liquid column chromatography (silica gel) using a chloroform:methanol gradient under low pressure (10 psi). The solvent is removed in vacuo and the product, MDP-aminocaproyl-DNDPE, characterized by phospholipase $A_2$ digestion, LSIMS, $H^1$-NMR, and IR.

Synthesis of mono(12-methacyloyl-3,6,9,12 -tetraoxadecylsuccinyl)-trehalose dimycolate (MTS-TDM):

MTS (0.1 mmol), ethylchloroformate (0.11 mmol), and triethylamine (0.11 mmol) are combined with dry dioxane (2.5 ml) and stirred at 23° C. After 1.5 hr the mixture is added dropwise to a stirring solution of TDM (0.1 mmol) prepared as described (Toubiana et al., *Carbohdr. Res.* (1975) 44:308; Azuma et al., *J. Natl. Cancer Inst.* (1974) 52:95–101; and Promé et al., *Eur. J. Biochem.* (1976) 63:543), and dry dichloromethane (10 ml). After 24 hr the solvent is removed in vacuo and the products separated by liquid column chromatography using a chloroform:methanol:water gradient as the eluent. Fractions containing only a single spot by thin-layer chromatography are dried in vacuo and characterized by LSIMS, $H^1$-NMR, and IR. Only the mono-MTS substituted TDM, mono(12 -methacryloyl-3,6, 9,12-tetraoxadecylsuccinyl)-trehalose dimycolate (MTS-TDM), is used for polymerized adjuvant systems below.

Polymerized Adjuvant Formulations

Formulation I: Polymerized vesicles containing MDP-aminocaproyl-DNDPE (0.01 mmol) and L-α-distearoylphosphatidylcholine (0.003 mmol) are prepared by methods described (Hub et al., *Angew. Chem. Int. Ed. Engl.* (1980) 19:938; Johnston et al., *Biochem. Biophys. Acta* (1980) 602:57; and Lopez et al., *J. Am. Chem. Soc.* (1982) 104:305), with modifications. The lipids are dissolved in chloroform:methanol (10 ml, 3:1 v/v) and dried into a thin film on the bottom of a round-bottom flask (50 ml) by rotoevaporation. The lipids are further dried in vacuo for 1 hr. Water or buffer (e.g. phosphate buffered saline) is added to bring the final concentration of lipid/water to 5–10 mg/ml. Vesicles are formed as described (see relevant literature above) by slowly warming the flask to a temperature greater than the melting transition of the lipids (>50° C.) for 1–2 hr, followed by gently stirring the solution, and then lowering the temperature below the melting transitions of the lipids (less than 20° C). Polymerization is performed as described (see relevant literature). Vesicles are characterized by electron microscopy, light scattering, and spectroscopic analysis. For the enhancement of antibody formation (see Biological Assays), antigen (1.5 parts by weight antigen to total weight of .polymer prepared above) is added prior to polymerization in one experiment and after polymerization in another experiment.

Formulation II: Polymerized vesicles containing copolymerized polyMTS-MPL (0.01 mmol based on monomer), polyMTS-TDM (0.01 mmol based on monomer), polysodium 2,3-bis (hexadecyl, oxy) -propyl-12-methacryloyl-3,6, 9,12 -tetraoxadecylphosphate (0.05 mmol based on monomer) prepared as described by Elbert et al. (1985), and poly-2-hydroxyacrylate (0.15–0.3 mmol) are prepared by methods described (Elbert et al. (1985) supra; and Laschewsky et al. (1986) supra) with modifications. The lipids and 2-hydroxyacrylate are dissolved in toluene (10 mg/ml final concentration) by warming and sonication. 2,2'-azoisobutyronitrile is added (0.01–0.2 mg/ml final conc.), the mixture flushed with nitrogen, and then polymerization is carried out at 60° C. for 20 hr. Polymers are precipitated with methanol:acetone, rinsed with methanol:acetone, and then liposomes prepared by the addition of water or buffer (1–5 mg/ml final concentration) and ultrasonication at 60° C. for 0.5 hr. Polymerized vesicles are characterized by electron microscopy, light scattering, and spectroscopic analysis. For the enhancement of antibody formation (see Biological Assays), antigen (1.5 parts by weight antigen to the total weight of adjuvant components prepared above) is added directly prior to sonication in one experiment and after sonication in another experiment.

Formulation III: Precipitated polymers of polyMDP-aminocaproyl-DNDPE (0.01 mmol based on monomer, prepared from polymerized vesicles of pure MDP-aminocaproyl-DNDPE as described in formulation I), polyMTS-TDM (0.01 mmol based on monomer, prepared as described in formulation II), poly-2,3 -bis(hexadecyloxy)propyl-12-methacryloyl-3,6,9,12-tetraoxadecylsuccinate (0.05 mmol based on monomer, prepared as described by Elbert et al. (1985)), and polyMTS-MPL (0.01 mmol based on monomer, prepared as in formulation II) are gently ground to an oily powder. Liposomes are prepared by the addition of water or buffer (1–5 mg/ml final concentration) and ultrasonication at 60° C. for 1 hr. Vesicles are characterized by electron microscopy, light scattering, and spectroscopic analysis. For the enhancement of antibody formation (see Biological Assays), antigen (1.5 parts by weight antigen to the total weight of adjuvant component prepared above) is added directly prior to vesicle formation in one experiment and after vesicle formation in a second experiment.

Formulation IV: Polymerized vesicles containing co-polymerized, polyMTS-MPL (0.01 mmol based on monomer), polyMTS-TDM (0.01 mmol based on monomer), polyN$^1$-(N-acetylmuramyl-L-alanyl-D-isoglutaminyl)-N$^6$ -acryloylhexamethylenediamine (0.01 mmol, based on monomer, prepared as described by Kohorlin and Abashev, Bioorg. Khim. (1984) 10(8):1119–1126), and acrylamide (0.1–0.5 mmol based on monomer) are prepared as in formulation II. For the enhancement of antibody formation (see Biological Assays), antigen (1.5 parts by weight antigen to total weight of adjuvant component prepared above) is added to the mixture of polymers directly prior to vesicle formation in one experiment and after vesicle formation in another experiment.

Formulation V: TDM (0.01 mmol, from sources cited in Synthesis of MTS-TDM), MPL (0.01 mmol, from sources cited in Synthesis of MTS-MPL), MDP-aminocaproyl-DNDPE (0.01 mmol, prepared as described earlier), and poly(12-methacryloyl-3,6,9,12-tetraoxadecyl)-3 -(N,N-dioctadecylcarbamoyl)-propionate (0.05–0.1 mmol based on monomer, prepared and polymerized as described by Elbert et al. (1985) supra) are dissolved in chloroform (25 ml) and dried into a thin film in the bottom of a round-bottom flask by rotoevaporation. The lipids are further dried in vacuo for 1 hr, and then slowly hydrated with water or buffer (5–10 mg/ml final concentration) at 70° C. for 1–2 hr. If any flocculent matter remains, the solution is further dispersed by sonication (1–30 min, 50° C.). For the enhancement of antibody formation (see Biological Assays), antigen (1.5 parts by weight antigen to the combined weights of TDM, MPL, and MDP-aminocaproyl-DNDPE as combined above) is added with the water or buffer prior to warming in one experiment and after warming in another experiment.

Formulation VI: Liposomes containing TDM (0.01 mmol, from sources cited in Synthesis of MTS-TDM), MPL (0.01 mmol, from sources cited in Synthesis of MTS-MPL), MDP-aminocaproyl-DNDPE (0.01 mmol, prepared as described earlier), and dimethyl-bis(2-octadeca-2,3 -dienoyloxyethyl)ammonium bromide (0.03 mmol, prepared as described by Gaub et al., Biophysics J. (1984) 45:725–731) are prepared as in formulation V with modifications. In one experiment, the vesicles are formed by hydration (5–10 mg total lipid per ml water) at 60° C. as described. After 1–2 hr the solution is gently stirred for 10 min, the temperature of the solution lowered to 15° C., the solution transferred to a quartz vial, and then polymerized by irradiation (254 nm) with a Pen-Ray-UV-Lamp (A. R. Vetter Co., Rebersburg, Pa.) for 1 hr. In a similar experiment, polymerization is carried out at 35° C. Vesicles are characterized by electron microscopy, light scattering, and spectroscopic analysis. For enhancement of antibody formation (see Biological Assays), antigen (1.5 parts by weight antigen to the combined weight of TDM, MPL, and MDP-aminocaproyl-DNDPE as prepared above) is added, in each experiment, to the lipid composition prior to hydration.

Formulation VII: The aqueous preparations of adjuvant formulations, I–VI, prepared with or without antigen (see respective formulations) are lyophilized to yield a paste-like powder. The powder (10 mg) is combined with squalene oil (80 μl) in the bottom of a dry glass tissue grinder tube (30 ml) and then ground with a snug-fitting teflon pestle (1000 rpm for 3 min) at 23° C. After grinding, 4 ml phosphate buffered saline, containing 0.2% Tween-80, is added and the polymerized adjuvant/oil/water mixture emulsified by further grinding (1000 rpm, 4 min). Aliquots of emulsion are vortexed and then used immediately (see Biological Assays).

Biological Assays

I. Enhancement of Resistance to Vital Infection. For protection against a mouse virulent strain of influenza A virus (A/PR/8/34(HINI)), polymerized adjuvant formulations I–VII are injected intravenously into C57BL/10× BALB/c mice via the method described by Mashihi et al., Int. J. Immunopharmac. (1986) 8:(3):339–345. In one experiment an aliquot of an adjuvant formulation (containing 450 μg adjuvant based on the total monomer composition of the adjuvants present) is injected intravenously into a mouse. After three weeks the mouse is infected by an aerosol spray of the virus (A/PR/8/84). Lung virus titres are determined 72 hr after the infection, as described by Mashihi et al. (above). In a second experiment, vital protein subunits (A/Victoria/3/75 and B/Hong Kong/5/72) are injected as antigen (4 μg per dose) intramuscularly in combination with a subject adjuvant formulation (total 300 μg adjuvant, based on the total monomeric adjuvant composition per dose). The mice are infected and assayed as described above.

II. Tumor Regression. Strain 2 guinea pigs bearing 6–7 day old line-10 tumors 8–10 mm in diameter (a transplantable hepatocellular carcinoma, see Rapp, Isr. J. Med. Sci. (1973) 9:366) are inoculated (intravenously in one experiment and intralesionally in another) with doses of adjuvant formulations I–VII (aqueous aliquots without antigen, 300 μg total adjuvant by weight, based on total of monomer adjuvant composition per dose). Animal cure rates are assessed according to Ribi et all, *Cancer Immunol. Immunother.* (1978) 3.:171–177. Animals are considered cured when the tumors completely disappear, metastases are not palpable at the first draining lymph node, and the guinea pigs reject a rechallenge of line-10 tumor transplantation.

III. Enhancement of Antibody Formation. Aliquots of an adjuvant formulation, I–VII (0.05–0.1 ml) , containing 200 μg total adjuvant (based on total weight of monomer adjuvant in the composition), and viral antigen (10 μg, A/Victoria/3/75), are combined as described (see Formulation), and then injected subcutaneously into C57BL/10×BALB/c mice. Antibody titres, to the vital subunits, are measured with the standard enzyme-linked immunosorbant assay (ELISA) after 14 and 31 days. In another experiment, compositions, identical to those described above, are injected intravenously, and then antibody titres measured after 14 and 31 days. Control experiemnts are performed in an identical manner but with no adjuvant present.

In accordance with the subject invention greatly enhanced immune responses can be achieved. By employing adjuvants in conjunction with a polymer, the adjuvant provides a simulation of a cell, which mimics the immune system activating effect of a microorganism. Different adjuvants can be employed for ease of preparation, compatibility with the antigen and degree of enhancement of immune response.

All publications and patent applications mentioned in this specification are indicative of the level of skill of those skilled in the art to which this invention pertains. All publications and patent applications are herein incorporated by reference to the same extent as if each individual publication or patent appliction was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. A method for producing an immune response in a vertebrate host, said method comprising administering to said host an immunogenic effective amount of an immunological composition comprising an antigen and a polymeric immunological adjuvant composition comprising:

a copolymer formed from the polymerization of monomers comprising at least one a water soluble addition polymerizable acrylyl or methacrylyl monomer having at least one adjuvent joined thereto through a linking group and a a water soluble addition polymerizable acrylyl or methacrylyl monomer having joined thereto a lamellar forming lipid comprising a chain of from 8 to not more than 36 carbon atoms;

said lipid adjuvant selected from the group consisting of monophosphoryl lipid A, lipopolysaccharide, BCG cell wall skeleton, diphosphoryl lipid A, muramyl di- or tripeptide, muramyl dipeptide-phosphatidyl-ethanolamine, muramyltripeptide phosphatidylcthanolamine, trehalose monomycolate, trehalose dimycolate, lipid X, isoprinosine, and lithosperman (A, B or C), wherein said lamellar forming lipid is present in a ratio of at least 1 lamellar forming lipid per 100 monomer units of said polymer.

2. A method according to claim 1, wherein said copolymer further comprises acrylyl or methacrylyl monomer units having side groups selected from the group consisting of hydroxyethyl, methyl, ethyl, 2-aminoethyl, and 2-ammoniumethyl.

* * * * *